US012558321B2

(12) United States Patent
Malhotra et al.

(10) Patent No.: US 12,558,321 B2
(45) Date of Patent: Feb. 24, 2026

(54) PHARMACEUTICAL FORMULATION

(71) Applicant: CIPLA LIMITED, Mumbai (IN)

(72) Inventors: Geena Vinod Malhotra, Mumbai (IN);
Preeti Prashant Raut, Mumbai (IN);
Vaibhav Panditrao Deshmukh, Airoli
(IN); Dipak Narayan Date, Thane (IN)

(73) Assignee: CIPLA LIMITED, Mumbai (IN)

( * ) Notice: Subject to any disclaimer, the term of this
patent is extended or adjusted under 35
U.S.C. 154(b) by 83 days.

(21) Appl. No.: 17/285,260

(22) PCT Filed: Oct. 15, 2019

(86) PCT No.: PCT/IN2019/050763
§ 371 (c)(1),
(2) Date: Apr. 14, 2021

(87) PCT Pub. No.: WO2020/079706
PCT Pub. Date: Apr. 23, 2020

(65) Prior Publication Data
US 2021/0346302 A1     Nov. 11, 2021

(30) Foreign Application Priority Data
Oct. 15, 2018     (IN) .............................. 201821039072

(51) Int. Cl.
*A61K 9/48*          (2006.01)
*A61K 31/496*        (2006.01)

(52) U.S. Cl.
CPC .......... *A61K 9/4825* (2013.01); *A61K 9/4858*
(2013.01); *A61K 9/4875* (2013.01); *A61K
31/496* (2013.01)

(58) Field of Classification Search
CPC .. A61K 9/4825; A61K 9/4858; A61K 9/4875;
A61K 31/496; A61K 47/44;
(Continued)

(56) References Cited

U.S. PATENT DOCUMENTS 5,536,729 A     7/1996   Waranis et al.
5,538,737 A     7/1996   Leonard et al.
(Continued)

FOREIGN PATENT DOCUMENTS

CN        102056598 A      5/2011
CN        105963268 A      9/2016
(Continued)

OTHER PUBLICATIONS

Flick, A. C., Ding, H. X., Leverett, C. A., Kyne Jr, R. E., Liu, K. K.
C., Fink, S. J., & O'Donnell, C. J. (2016). Synthetic approaches to
the 2014 new drugs. Bioorganic & Medicinal Chemistry, 24(9),
1937-1980. (Year: 2016).*
(Continued)

*Primary Examiner* — Frederick F Krass
*Assistant Examiner* — Lucy M Tien
(74) *Attorney, Agent, or Firm* — Conley Rose, P.C.;
Rodney B. Carroll

(57)     ABSTRACT

Soft gelatin capsules comprising a suspension composition
of nintedanib or a pharmaceutically acceptable salt thereof
in medium chain triglycerides and carrier system, wherein
the carrier system comprises solubilizers, phospholipids,
thickeners and mixtures thereof.

13 Claims, 2 Drawing Sheets

Dissolution of marketed formulation and formulation of example 1 in GB pH 1.2

(58) Field of Classification Search
CPC ........ A61K 9/10; A61K 9/4866; A61K 47/08; A61K 47/26; A61K 47/10; A61K 47/12; A61K 47/14
USPC ........................................................ 424/456
See application file for complete search history.

(56) References Cited

U.S. PATENT DOCUMENTS

| | | | |
|---|---|---|---|
| 5,645,856 | A | 7/1997 | Lacy et al. |
| 6,309,663 | B1 | 10/2001 | Patel et al. |
| 6,464,987 | B1 | 10/2002 | Fanara et al. |
| 9,907,756 | B2 | 3/2018 | Messerschmid et al. |
| 2004/0063794 | A1 | 4/2004 | Schwarz et al. |
| 2007/0104780 | A1* | 5/2007 | Lipari .................. A61K 31/501 514/273 |
| 2010/0178335 | A1* | 7/2010 | Echanagorria .......... A61P 29/00 424/455 |
| 2011/0301177 | A1* | 12/2011 | Messerschmid ..... A61K 9/4858 206/524.6 |

FOREIGN PATENT DOCUMENTS

| | | |
|---|---|---|
| CN | 0108078952 A | 5/2018 |
| CN | 107184549 B | 11/2020 |
| EA | 029996 B1 | 6/2009 |
| IN | 201821039072 | 10/2018 |
| WO | 2009147212 A1 | 12/2009 |
| WO | 2019106692 A1 | 6/2019 |
| WO | 2019197961 A1 | 10/2019 |
| WO | 2020079706 A1 | 4/2020 |

OTHER PUBLICATIONS

Guo Y, Luo J, Tan S, Otieno BO, Zhang Z. The applications of Vitamin E TPGS in drug delivery. Eur J Pharm Sci. 2013;49(2):175-186. doi:10.1016/j.ejps.2013.02.006 (Year: 2013).*

"Types of Powders—Unacademy." Unacademy, Aug. 23, 2023, unacademy.com/content/nta-ugc/study-material/pharmaceutical-analysis/types-of-powders. (Year: 2023).*

Foreign Communication from a related application—International Search Report and Written Opinion of International Application No. PCT/IN2019/050763, dated Feb. 12, 2020, 13 pages.

Foreign Communication from Related Application—CN Decision of Rejection, Chinese Patent Application No. 201980075716.9, dated Jun. 29, 2023, 12 pages.

Foreign Communication from a related application—Office Action and Search Report of RU Patent Application No. 2021113529 dated Aug. 8, 2023. With English translation, 20 pages.

Mitrovic, Jelena R., "High amount of lecithin facilitates oral delivery of a poorly soluble pyrazoloquinolinone ligand formulated in lipid nanoparticles: Physicochemical, structural and pharmacokinetic performances." Elsevier Manuscript,. 2023, 48 pages, retrieved from https://www.sciencedirect.com/science/article/pii/S0378517323000339.

* cited by examiner

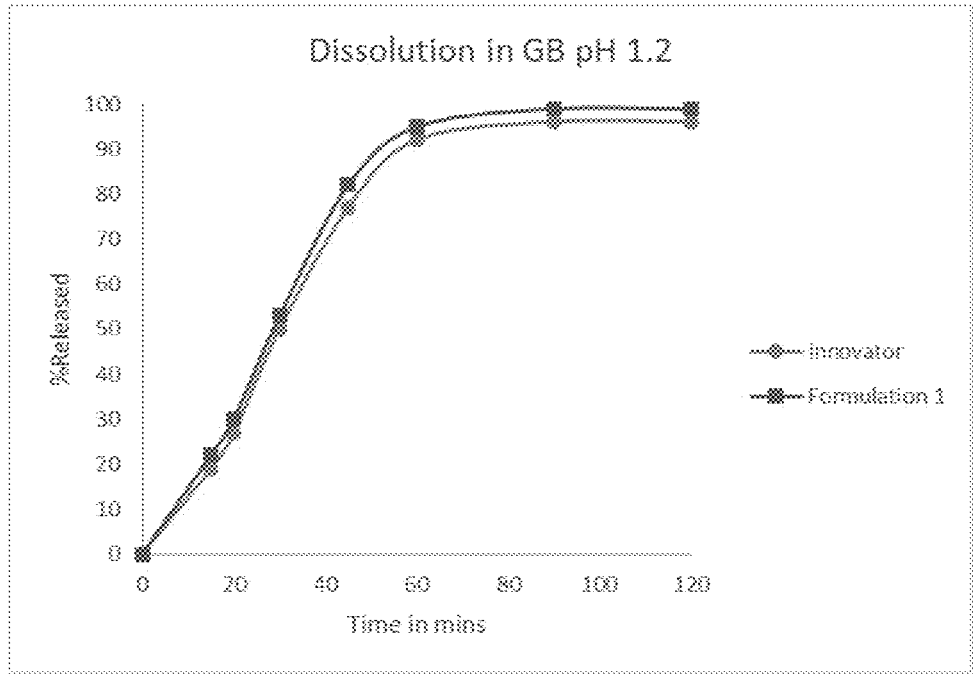
Fig 1: Dissolution of marketed formulation and formulation of example 1 in GB pH 1.2

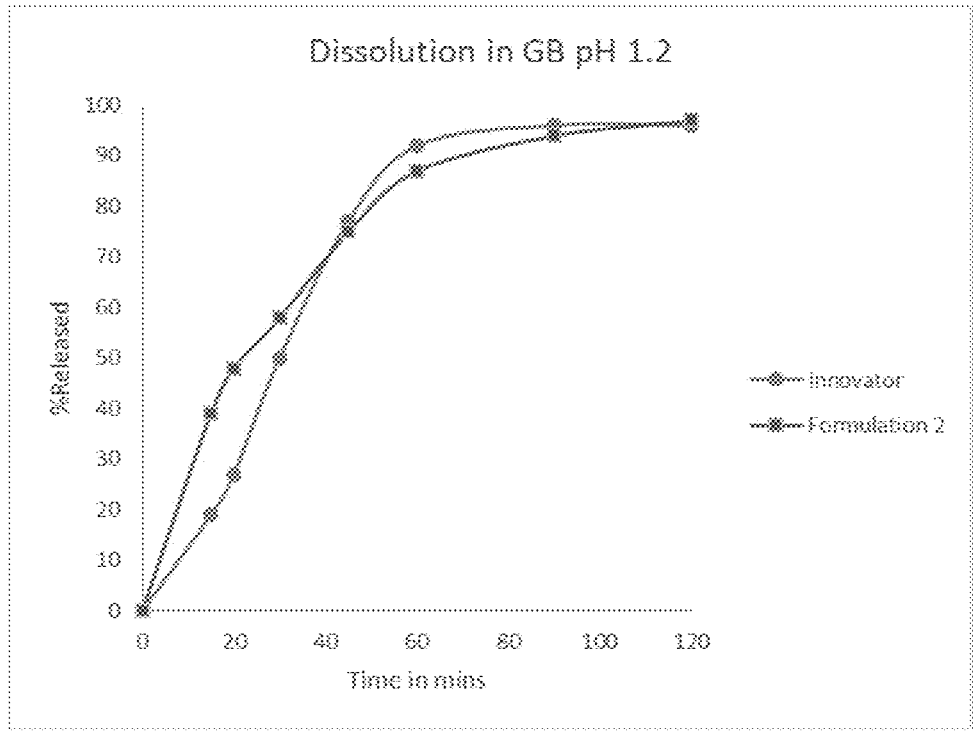
Fig 2: Dissolution of marketed formulation and formulation of example 3 in GB pH 1.2

PHARMACEUTICAL FORMULATION

CROSS-REFERENCE TO RELATED APPLICATIONS

This Application is a filing under 35 U.S.C. 371 of International Application No. PCT/IN2019/050763 filed Oct. 15, 2019, entitled "Pharmaceutical Formulation," which claims the benefit of Indian Application 201821039072 filed Oct. 15, 2018, both of which are hereby incorporated by reference in their entirety.

FIELD OF INVENTION

The present invention relates to soft gelatin capsules consisting of capsule shell and capsule filling. More particularly, the capsule filling is pharmaceutical formulation comprising of nintedanib or its pharmaceutically acceptable salts, medium chain triglyceride, at least one carrier system and pharmaceutically acceptable excipients thereof. There is also provided a process of preparing the formulation and the use of the said formulation thereof in the treatment and/or prevention of idiopathic pulmonary fibrosis.

BACKGROUND OF INVENTION

Idiopathic pulmonary fibrosis is a chronic progressive disease characterized by unclear etiology and progressive fibrotic lesions in the lungs. It is the most common idiopathic interstitial pneumonia. There are currently no preventive methods or internationally recognized treatments with specific curative effects other than lung transplantation. The global prevalence rate is 14-43 cases/100,000 people. Due to rapid progress and poor prognosis, the disability and mortality of the disease are extremely high. The average life expectancy of the patient is 3-5 years after diagnosis, or 4-6 years after the onset of symptoms. For a long time, idiopathic pulmonary fibrosis, like other interstitial pneumonia, was considered to be an inflammatory disease of the lungs. However, with the deepening of its pathogenesis research, the treatment strategy has shifted from anti-inflammatory to the specific aspects of the pathophysiology of idiopathic pulmonary fibrosis.

Nintedanib is a triple tyrosine kinase inhibitor and growth factor antagonist used for the treatment of idiopathic pulmonary fibrosis. Nintedanib plays a role in growth factor receptors that have been shown to have potential effects in the pathogenesis of pulmonary fibrosis. The most important of these are platelet-derived growth factor receptor (PDGFR), fibroblast growth factor receptor (FGFR), and vascular endothelial growth factor receptor (VEGFR).

Nintedanib esylate has a chemical name ethanesulfonic acid—methyl (3Z)-3-{[(4-{methyl-[(4-methylpiperazin-1-yl)acetyl]amino}phenyl)amino]-(phenyl)methylidene}-2-oxo-2,3-dihydro-1H-indole-6-carboxylate (1:1) and has the following chemical structure: Nintedanib or its pharmaceutically acceptable salt especially esylate salt has a poor solubility at neutral conditions, resulting in a lower bioavailability of only 4.7%, which greatly limits its clinical application.

It is difficult to formulate drugs of low water solubility, for example those having solubility of less than about 1 part per 10,000 parts water for oral delivery and low bioavailability. In such cases where the API's are poorly water-soluble, conventional formulation strategies are no longer adequate or useful to achieve the acceptable solubility and in turn bioavailability. Although, a number of alternative technologies are being developed, lipid-based formulations have always seemed promising in enhancing the oral bioavailability of such lipophilic drugs. Such formulations commonly make use of excipients which are either liquid or semi-solid in nature. Some of the solutions to the challenge of low oral bioavailability have been proposed for particularly poorly soluble drugs. For example, U.S. Pat. No. 5,645,856 proposes formulating a hydrophobic drug with an oil, a hydrophilic surfactant and a lipophilic surfactant that substantially reduces an inhibitory effect of the hydrophilic surfactant on in vivo lipolysis of the oil, such lipolysis being said to be a factor promoting bioavailability of the drug.

U.S. Pat. No. 6,309,663 proposes pharmaceutical compositions comprising a combination of surfactants said to enhance bioabsorption of a hydrophilic therapeutic agent. Phospholipids such as phosphatidylcholine are again listed among exemplary surfactants.

U.S. Pat. No. 6,464,987 proposes a fluid pharmaceutical composition comprising an active substance, 3% to 55% by weight of phospholipid, 16% to 72% by weight of solvent, and 4% to 52% by weight of fatty acid.

U.S. Pat. No. 5,538,737 proposes a capsule containing a water-in-oil emulsion wherein a water-soluble drug salt is dissolved in the water phase of the emulsion and wherein the oil phase comprises an oil and an emulsifying agent. Among oils mentioned are medium chain triglycerides; among emulsifying agents mentioned are phospholipids such as phosphatidylcholine.

US2004/0063794 and U.S. Pat. No. 5,536,729 proposes an oral formulation comprising rapamycin, at a concentration of about 0.1 to about 50 mg/ml, in a carrier comprising a phospholipid solution.

In case of nintedanib, considering the solubility and bioavailability of the drug, some attempts have been made to improve the solubility of nintedanib and provide pharmaceutical formulations. U.S. Pat. No. 9,907,756 discloses a capsule containing lipid suspension of the nintedanib in 1 to 90 wt % of medium chain triglycerides, 1 to 30 wt % of hard fat and 0.1 to 10 wt % of lecithin. However, the release of drug from the formulation is affected by single carrier excipient or mixture of carrier excipient and their amount in the formulation. The physical stability of the suspension formulation is affected by factors such as sedimentation rate caking etc.

CN108078952 discloses soft capsule comprising suspension of nintedanib ethanesulfonate having the size distribution range of the D90 from 40 µm to 80 µm. The reduction of particle size of active, its incorporation in the formulation, and the maintenance of the size needs special process of manufacture and is costly. Also, the dissolution profile solely depends on particle size of active.

CN107184549 provides a capsule containing nintedanib self micro-emulsion wherein the droplet size of the micro-emulsion is between 10 and 100 nm and the carrier medium is designed to spontaneously form an emulsion in the stomach thereby facilitating absorption of nintedanib. These systems are self micro emulsifying drug delivery system (SMEDDS). A major drawback of such system is that they have to be accurately prepared and even slight variation in composition will not lead to formation of emulsion in the stomach and thus destroying its beneficial properties. Also, controlling the particle size of active plays a major role in the system.

CN105963268 discloses dispersible tablet comprising nintedanib and other pharmaceutically acceptable excipients necessary for dispersion of tablet. The drugs having low solubility may not dissolve in the excipients of the conventional dosage form and thus leading to no content uniformity and high content deviation. Also, the dispersible tablets release actives quickly effecting the pharmacologic effect of the formulation.

Although the prior arts disclose different types of compositions which address the solubility issues of nintedanib, most of these solubility enhancing techniques involve critical and tedious manufacturing process, make use of many excipients or are modified according to the specific physicochemical characteristics of nintedanib.

Hence, there is a need to develop a dosage form of nintedanib, which overcome the drawbacks of prior available formulations, has good physical stability, is cost effective, can be produced by simple manufacturing techniques and can maximize the solubility of nintedanib from such dosage form as well as improve its bioavailability.

OBJECT OF INVENTION

An object of the present invention is to provide soft gel capsule formulation comprising a suspension of nintedanib or its pharmaceutically acceptable salt and a carrier system having improved solubility and bioavailability.

Another object of present invention is to provide a pharmaceutical composition comprising nintedanib or its pharmaceutically acceptable salt with a substantially non-aqueous carrier system and optionally pharmaceutically acceptable excipients.

Another object of the present invention is to provide a process for preparing a pharmaceutical composition comprising nintedanib or its pharmaceutically acceptable salts, solvates, hydrates, esters, derivatives, and one or more pharmaceutically acceptable excipients thereof.

Another object of the present invention is to provide a method for treatment of idiopathic pulmonary fibrosis administering a pharmaceutical composition comprising nintedanib or its pharmaceutically acceptable salts, solvates, hydrates, esters, derivatives, and one or more pharmaceutically acceptable excipients thereof.

SUMMARY OF INVENTION

According to an aspect of present invention, a soft gel capsule composition is provided comprising suspension composition of nintedanib or its pharmaceutically acceptable salt and carrier system having improved solubility and bioavailability.

According to other aspect of present invention, there is provided a pharmaceutical composition comprising nintedanib with a substantially non-aqueous carrier system and optionally pharmaceutically acceptable excipients.

According to another aspect, there is provided a process of manufacturing pharmaceutical composition comprising nintedanib or its pharmaceutically acceptable salts, solvates, hydrates, esters, derivatives, and one or more pharmaceutically acceptable excipients thereof.

According to yet another aspect, there is provided a method of treating idiopathic pulmonary fibrosis administering a pharmaceutical composition comprising nintedanib or its pharmaceutically acceptable salts, solvates, hydrates, esters, derivatives, and one or more pharmaceutically acceptable excipients thereof.

According to another aspect, there is provided a use of the pharmaceutical composition comprising nintedanib or its pharmaceutically acceptable salts, solvates, hydrates, esters, derivatives, and one or more pharmaceutically acceptable excipients thereof in the manufacture of a medicament for treating idiopathic pulmonary fibrosis.

BRIEF DESCRIPTION OF THE FIGURES

FIG. 1 indicates dissolution profile of marketed formulation and formulation of present invention of example 1.

FIG. 2 indicates dissolution profile of marketed formulation and formulation of present invention example 3.

DETAILED DESCRIPTION OF INVENTION

Nintedanib is slightly soluble in water, therefore, formulating a suitable composition of nintedanib which is easy to manufacture as well as which alleviates the solubility and bioavailability problems is a challenge. Carrier system plays a major role in formulation of low water soluble drug as it affects the physical stability of formulation, dissolution and release of active from the formulation at a desired rate.

Thus, the inventors after rigorous experimentation have found that the solubility properties and bioavailability of nintedanib can be improved by developing a liquid and/or semi-solid compositions preferably suspension formulation of nintedanib with a suitable carrier system. The inventors of the present invention after screening a range of carrier systems have developed a pharmaceutically acceptable liquid and/or semi-solid dosage form comprising nintedanib in optimum amount of suitable carrier system.

The term "Nintedanib" is used in broad sense to include not only "Nintedanib free base" per se but also its pharmaceutically acceptable salts, pharmaceutically acceptable solvates, pharmaceutically acceptable hydrates, pharmaceutically acceptable esters, pharmaceutically acceptable enantiomers, pharmaceutically acceptable derivatives, pharmaceutically acceptable polymorphs, pharmaceutically acceptable prodrugs, pharmaceutically acceptable complexes etc.

The term "salt" as used herein, refers to salts derived from inorganic or organic acids.

Examples of suitable salts include, but are not limited to, acetate, adipate, alginate, citrate, aspartate, benzoate, benzenesulfonate, bisulfate, butyrate, camphorate, camphorsulfonate, digluconate, cyclopentanepropionate, dodecylsulfate, esylate or ethanesulfonate, glucoheptanoate, glycerophosphate, hemisulfate, heptanoate, hexanoate, fumarate, hydrochloride, carbonates, bicarbonates, hydrobromide, hydrolodide, 2-hydroxy-ethanesulfonate, lactate, maleate, mandelate, methanesulfonate, nicotinate, 2-naphthalenesulfonate, oxalate, palmoate, pectinate, persulfate, 2-phenylpropionate, picrate, pivalate, propionate, salicylate, succinate, sulfate, nitrates, tartrate, sulfonates, thiocyanate, tosylate, mesylate, and undecanoate. Preferably, the salt used in present formulation is nintedanib esylate salt.

According to one embodiment, the pharmaceutical formulation of present invention, may comprise therapeutically effective amount of nintedanib esylate in an amount from about 20% to 60% w/w, preferably 25% to 55% w/w, preferably 30% to 50% w/w of total weight of formulation. Most preferably, the nintedanib esylate is present at 43% w/w of total weight of formulation.

The term "pharmaceutically acceptable" mentioned throughout the specification would be applied to a carrier, diluent or excipient which is compatible with the actives as employed.

The terms "oral administration" and "orally administered" herein refer to administration to a subject per os, that is, administration wherein the composition is immediately swallowed. "Oral administration" is distinguished herein from intraoral administration, e.g. sublingual or buccal administration or topical administration to intraoral tissues such as periodontal tissues, that does not involve immediate swallowing of the composition.

The term "suspension" refers to a heterogeneous mixture of solid particles and liquid.

A "carrier system" herein comprises a component in which nintedanib salt is homogeneously distributed therein. In preferred embodiment, the drug-carrier system is encapsulated within a capsule shell that is suitable for oral administration. The carrier is "substantially non-aqueous", i.e., having no water, or in an amount of 0% to less than about 5% by weight.

The carrier system of the formulation of present invention comprises of medium chain triglycerides, phospholipids, solubilizing agent, surfactant, emulsifying agents or mixture thereof which solubilizes the drug or provide enhanced solubilization of the drug, additionally present are viscosity adjusting agents. The ingredients of carrier system play an important role in formulation since nintedanib is a drug having low solubility.

The medium chain triglycerides present in the carrier system are selected from triglycerides of saturated fatty acids containing 8 to 10 carbon atoms. Suitable glyceride materials include, without limitation, medium to long chain mono-, di- and triglycerides. Thus, glyceride materials comprising caprylyl and capryl chains, e.g. caprylic/capric mono-, di- and triglycerides, are examples of "medium chain" glyceride materials herein. A suitable example of a medium chain triglyceride material is a caprylic/capric triglyceride product such as, Captex 355 EP™, Miglyol 812N and products substantially equivalent thereto. Suitable examples of long chain triglycerides include any pharmaceutically acceptable vegetable oil, for example canola, coconut, corn, flaxseed, safflower, soy and sunflower oils, and mixtures of such oils. In an embodiment, the triglycerides are present in an amount of about 10% to 80% w/w, about 15% to 70% w/w of the formulation. Preferably, the medium chain triglycerides are present in an amount of 25% to 40% w/w of total formulation.

The phospholipids that can be used in the formulation of present invention are phosphoric acid esters that yield on hydrolysis phosphoric acid, fatty acid(s), an alcohol and a nitrogenous base. The phospholipids that can be used in the formulation of present invention are selected from, but not limited to, phosphatidylcholines, phosphatidylserines, phosphatidylethanolamines and the mixtures thereof. In one embodiment, the composition comprises mixtures of glycerophospholipids including phosphatidylcholine, phosphatidylethanolamine, phosphatidylinositol, phosphatidylserine, and phosphatidic acid and is known as lecithin. The lecithins used in present invention are derived from animal sources such as egg yolk, but plant sources are generally preferred. Soy is a particularly rich source of lecithin that can provide phosphatidylcholine for use in the present invention.

In an embodiment, the amount of lecithin incorporated in the formulation of present invention is from about 0.1% to 35% w/w of total formulation, more preferably from about 1% to 30% w/w of formulation, most preferably from about 0.5% to 25% w/w of formulation. In a most preferred embodiment, lecithin is incorporated in an amount of 11% to 20% w/w of total formulation.

Suitable solubilizing agents that may be employed in the pharmaceutical composition comprising capsules of nintedanib include, but are not limited to, lineleoyl polyoxyl-6-glycerides, corn oil mono glycerides, corn oil di glycerides, corn oil triglycerides or mixtures thereof. In another embodiment the carrier comprises Gelucire® 44/14. Gelucire® 44/14. Suitable glycols which can be included are propylene glycol and polyethylene glycols (PEGs) having molecular weight of about 200 to about 1,000 g/mol. e.g., PEG 400, which has an average molecular weight of about 400 g/mol. In one embodiment, therefore, one or more glycols are present in a total glycol amount of at least about 1% but less than about 50% w/w, for example less than about 30%, less than about 20%, less than about 15% or less than about 10% by weight of the carrier system. In another embodiment, the carrier comprises substantially no glycol.

Suitable surfactant that may be employed in the pharmaceutical composition comprising capsules of nintedanib include, but are not limited to, amphoteric, non-ionic, cationic or anionic surfactants, such as, but not limited to, polyoxyethylene castor oil derivatives (for example, polyoxyethyleneglyceroltriricinoleate or polyoxyl ethylene castor oil (or polyoxyethylene glycerol oxystearate, glycerol polyethylene glycol oxystearate, polyethylene glycol hydrogenated castor oil, or block copolymers of ethylene oxide and propylene oxide, also known as polyoxyethylene polyoxypropylene block copolymers or polyoxyethylene polypropylene glycol, or a mono fatty acid ester of polyoxyethylene sorbitan, polyoxyethylene sorbitan monostearate, polyoxyethylene sorbitan monopalmitate, polyoxyethylene sorbitan monolaurate, propylene glycol monolaurate, propylene glycol dicaprylate/dicaprate or a sorbitan fatty acid ester (including sorbitan laurate, sorbitan monostearate, caprylocaproyl macrogolglyceride (Labrasol), octadecanoic acid (Labrafil) sorbitan oleate, sorbitan palmitate, sorbitan stearate), propylene glycol monocaprylate, soyabean oil, vegetable oil, triacetin, triethyl citrate, macrogolglycerol-hydroxystearate (traded for example under the name Eumulgin® HRE 40 PH) or macrogolglycerol-ricinoleate (also known as polyoxyl castor oil and traded for example under the name Cremophor® EL, Cremophor® RH40 or Eumulgin® RO 35 PH) or mixtures thereof. Preferably, Polyoxyl castor oil (Kolliphor EL), caprylocaproyl macrogolglyceride (Labrasol), octadecanoic acid (Labrafil) is used in an amount of 10% to 30% w/w of formulation. The terms solubilizing agent, surfactant and emulsifying agents can be used interchangeably in the specification.

Even when a sufficient amount of a glycol or glyceride material is present to solubilize the drug, the resulting carrier solution and/or the drug-carrier system may be rather viscous and difficult or inconvenient to handle. In such cases a viscosity adjusting agent or a thickener in an amount effective is added to the carrier system to provide acceptably desired viscosity. In a preferred embodiment, hard fat (Softisan 378) is used in the formulation of present invention. Some other examples of thickener are semisolid polyethylene glycols, preferably polyethyleneglycol 4000, or oleogel forming excipients, such as colloidal silica or bentonite, or bees wax, glycerol monostearate, hydrogenated vegetable oil, partially hydrogenated vegetable oil or hard fats. Some other viscosity enhancing/thickening agents, which may be used in the pharmaceutical composition of the present invention, include, but are not limited to methylcellulose, hydroxyethylcellulose, hydroxypropylcellulose, hydroxypropylmethylcellulose, hydroxy ethyl propyl cellulose, starches (such as maize or corn starch, potato starch, rice starch, tapioca starch, and wheat starch), carboxyvinyl polymers (carbomers such as Carbopol®), carboxymethyl cellulose and salts thereof, microcrystalline cellulose and arabic gum, guar gum, and xanthan gum and mixtures thereof. The preferred thickener is hard fat in an amount of 10% to 30% of total formulation.

In an embodiment, pre-blended products containing a suitable phospholipid and solubilizing agent combination can be included in formulation of the present invention. Some of the pre-blended mixtures of phospholipid and solubilizing agent product that can be included in formulation of present invention are Phosal 50 PG™, Phosal 53 MCT™, Phosal 50 SA+™ and mixtures thereof. The phosphatidylcholine component of these pre-blended products is derived from soy lecithin. A pre-blended product such as Phosal 50 PG™, Phosal 53 MCT™ or Phosal 50 SA+™ can, in some embodiments, constitute substantially the entire carrier system for a drug of low water solubility. In other embodiments, additional ingredients are present, for example ethanol (additional to any that may be present in the pre-blended product), non-phospholipid surfactant such as polysorbate 80, polyethylene glycol and/or other ingredients. In an embodiment, Phosal 53 MCT™ or a preblended product substantially equivalent thereto is included in the carrier in an amount of about 0.5% to 65%, about 1% to 50% w/w of the formulation.

The carrier system further may also comprise a pharmaceutically acceptable nonphospholipid surfactant such as polysorbate 80, polysorbate 20, Vitamin E TPGS, d-a-tocopheryl polyethylene glycol 1000 succinate can be included in an amount of 1% to about 25% w/w of the formulation.

In one aspect of the present invention, the pharmaceutical composition may comprise excipients enabling the capsules to be resistant to gastric juices and to be soluble in the intestine which have an enteric polymer coating. Examples of such additional excipients which can be included in formulation of present invention are diluents such as lactose, starches, silicon dioxide, etc., and polymers such as polyacrylates, high molecular weight PEGs, or cellulose derivatives, e.g. hydroxypropylmethylcellulose (HPMC) or mixtures thereof.

The term "liquid and/or semi-solid' mentioned throughout the specification refer to nintedanib and optionally, one or more pharmaceutically acceptable excipients, in the form of solution and/or partially in the form of finely divided particles suspended freely in a suitable vehicle and encapsulated in a soft and hard gelatin capsules.

Soft gelatin capsules are a suitable dosage form for the administration of liquids, suspensions, pastes and the like. Soft gelatin capsules are an effective delivery system, especially for poorly soluble drugs, because the capsules can contain liquid and/or semi-solid ingredients that help increase solubility or permeability of the drug across the membranes in the body. Such liquid and/or semi-solid ingredients are difficult to include in any other solid dosage form such as a tablet.

According to one embodiment, the present invention provides a suspension composition of nintedanib or its pharmaceutically acceptable salt with suitable carrier system filled in a shell comprising gelatin, carrageenan or HPMC.

In a preferred embodiment of the present invention, the formulation of present invention comprises of a suspension of therapeutically effective amount of nintedanib, 11% w/w lecithin, hard fat, medium chain triglycerides filled in a gelatin capsule shell.

In yet another preferred embodiment of the present invention, the formulation of present invention comprises of a liquid mix comprising therapeutically effective amount of nintedanib, polyoxyl castor oil, hard fat, medium chain triglycerides filled in a gelatin capsule shell.

In an embodiment, the dissolution profile of formulations of present invention is comparable with the dissolution profile of marketed formulation In other words, nintedanib may be partially in the form of solution and/or partially in the form of finely divided particles suspended freely in the liquid and/or semi-solid which makes nintedanib readily absorbed the moment the intestinal soluble gelatin, carrageenan or HPMC shell is dissolved.

The pharmaceutical composition, of the present invention, alleviates the solubility and bioavailability problems of nintedanib and is advantageous over the existing dosage forms of nintedanib.

The present invention thus further provides a pharmaceutical composition comprising nintedanib in the form of capsules made of gelatin, carrageenan or HPMC optionally with one or more pharmaceutically acceptable excipients.

According to another embodiment of the present invention, the pharmaceutical composition comprising capsules of nintedanib may comprise a therapeutically effective amount of nintedanib which is less than the conventionally administered daily dose.

In another aspect of the present invention, the pharmaceutical composition of the present invention may also be formulated in a suitable oral liquid dosage form, including, but not limited to emulsions, solutions, suspensions, syrups, and elixirs.

Poorly water-soluble drugs often require high doses in order to reach therapeutic plasma concentrations after oral administration. Improvement in the extent and rate of dissolution is highly desirable as this can lead to more reproducible oral bioavailability, subsequently leading to dose reduction and more reliable therapy.

Physical modifications of the drug particles such as micronization aim to increase the surface area, solubility and/or wettability of the powder particles. Micronization is used to elevate drug activity by increasing particle surface or by allowing active substances to reach their site of action by reducing particle size. The active in micronized form can be obtained by any of the processes such as, but not limited to, ball milling, jet milling, sonication, homogenization and solvent precipitation.

The pharmaceutical composition of the present invention may also comprise the active in a nanosized form. The nanoparticles of the present invention can be obtained by any of the processes such as, but not limited to, milling, precipitation, homogenization, high pressure homogenization, spray drying, spray-freeze drying, supercritical fluid technology, double emulsion/solvent evaporation, PRINT (Particle replication in non-wetting templates), thermal condensation and ultrasonication.

The present invention also provides a process to manufacture the pharmaceutical composition according to the present invention. The lipid suspension formulation may be prepared by conventional methods of producing formulations known from the literature i.e. by mixing the ingredients at a pre-determined temperature in a pre-determined order in order to obtain homogenized suspension. Particularly, during the preparation of a lipid suspension formulation of present invention and hard fat and parts of Medium-chain triglycerides are pre-mixed in the processing unit. Subsequently lecithin, the rest of medium-chain triglycerides and the active substance are added. The suspension is mixed, homogenized, de-aerated and finally sieved to produce the formulation (Fillmix). The gelatin basic mass components are mixed and dissolved at elevated temperature. After adjustment of the encapsulation machine, fill mix is processed into soft gelatin capsules using the rotary-die process. After encapsulation, the traces of the lubricant medium-chain triglycerides are removed from the capsule surface, using ethanol denatured with acetone, containing small quantities of Phosal® 53 MCT, used here as anti-sticking agent. The initial drying is carried out using a rotary dryer. For the final drying step, capsules are placed on trays. Drying is performed at 15-26° C. and low relative humidity. After 100% visual inspection of the capsules for separation of deformed or leaking capsules, the capsules are size sorted and further washed using ethanol denatured with acetone. Finally, the capsules are imprinted, using an Offset printing technology or an Ink-jet printing technology. Alternatively, the capsule imprint can be made using the Ribbon printing technology.

The present invention also provides a method of treating idiopathic pulmonary fibrosis which method comprises administration of a therapeutically effective amount of a pharmaceutical composition according to the present invention.

The present invention also provides a use of the pharmaceutical composition in the manufacture of a medicament for the treatment of idiopathic pulmonary fibrosis.

EXAMPLES

The following examples are for the purpose of illustration of the invention only and are not intended in any way to limit the scope of the present invention.

Example 1

Formulation 1 of Nintedanib Soft Gel Capsule

TABLE 1

| Sr. No. | Ingredient | Weight (mg) |
|---|---|---|
| 1 | Nintedanib | 50-300 |
| 2 | Polyoxyl castor oil (Kolliphor ® EL) | 1-500 |
| 3 | Hard Fat (Softisan 3 78) | 10-200 |
| 4 | Medium chain triglycerides (Miglyol 812N) | 30-500 |
| | Medicament weight | 100-1000 mg |
| 5. | Gelatin | 20-750 |
| 6. | Glycerin | 10-375 |
| 7. | Colouring agent | 0.02-75 |
| 8. | Purified Water | q.s |

Process

The excipients were dispensed and mixed in a jacketed manufacturing vessel for suitable time. The blend was homogenized at preselected set parameters. The gelatin shells were manufactured in suitable jacketed manufacturing vessel. The soft gelatin capsule was filled using encapsulation machine with the blend.

Example 2

In Vitro Dissolution of Nintedanib Soft Gelatin Capsule

The comparative in-vitro dissolution data of marketed formulation and the formulation of example 1 (formulation 1) in Dissolution Media as USP Type II/900 ml GB pH 1.2/35 rpm/37° C./120 min and Infinity at 200 RPM for 10 min is shown below in table 2:

TABLE 2

| Time interval (min.) | Marketed formulation | Formulation of example 1 |
|---|---|---|
| 15 | 19 | 22 |
| 20 | 27 | 30 |
| 30 | 50 | 53 |
| 45 | 77 | 82 |
| 60 | 92 | 95 |
| 90 | 96 | 99 |
| 120 | 96 | 99 |

Conclusion: Thus, it is concluded that the release profile of formulation of present invention comprising Kolliphor® EL showed comparative dissolution profile to Marketed formulation.

Example 3

Formulation 2 of Nintedanib Soft Gel Capsule

TABLE 3

| Sr. No. | Ingredient | Weight (mg) |
|---|---|---|
| 1. | Nintedanib | 50-300 |
| 2. | Phosal ® 53 MCT | 1-500 |
| 3. | Hard Fat (Softisan 3 78) | 10-200 |
| 4. | Medium chain triglycerides (Miglyol 812N) | 30-500 |
| | Medicament weight | 100-1000 mg |
| 5. | Gelatin | 20-750 |
| 6. | Glycerin | 10-375 |
| 7. | Colouring agent | 0.02-75 |
| 8. | Purified Water | q.s |

Process

The excipients were dispensed and mixed in a jacketed manufacturing vessel for suitable time. The blend was homogenized at preselected set parameters. The gelatin shells were manufactured in suitable jacketed manufacturing vessel. The soft gelatin capsule was filled using encapsulation machine with the blend.

Example 4

In Vitro Dissolution of Nintedanib Soft Gelatin Capsule

The comparative in-vitro dissolution data of marketed formulation and the formulation of example 3 (formulation 2) in Dissolution Media as USP Type II/900 ml GB pH 1.2/35 rpm/37° C./120 in and Infinity at 200 RPM for 10 min is shown below in table 4:

TABLE 4

| Time interval (min.) | Marketed formulation | Formulation 2 of example 3 |
|---|---|---|
| 15 | 19 | 39 |
| 20 | 27 | 48 |
| 30 | 50 | 58 |
| 45 | 77 | 75 |

TABLE 4-continued

| Time interval (min.) | Marketed formulation | Formulation 2 of example 3 |
|---|---|---|
| 60 | 92 | 87 |
| 90 | 96 | 94 |
| 120 | 96 | 97 |

Conclusion: Thus, it is concluded that the release profile of formulation of present invention comprising Phosal® 53 MCT showed comparative dissolution profile to Marketed formulation.

Example 5

Formulation 3 of Nintedanib Soft Gel Capsule

TABLE 5

| Sr. No. | Ingredients | Amount (%) |
|---|---|---|
| | MIX | |
| 1. | Nintedanib | 43.00 |
| 2. | Lecithin | 11.00- |
| 3. | Hard Fat (Softisan 378) | 20.00 |
| 4. | Medium chain Triglycerides (Miglyol 812N) | 30.00 |
| | Medicament weight | 100 |

Process of Preparation:

The excipients were dispensed and mixed in a jacketed manufacturing vessel for suitable time. The blend was homogenized at preselected set parameters. The gelatin shells were manufactured in suitable jacketed manufacturing vessel. The soft gelatin capsule was filled using encapsulation machine with the blend.

Example 6

In Vitro Dissolution of Nintedanib Soft Gelatin Capsule

The comparative in-vitro dissolution data of marketed formulation and the formulation of example 5 (formulation 3) in Dissolution Media as USP Type II/900 ml GB pH 1.2/35 rpm/37° C./120 in and Infinity at 200 RPM for 10 min is shown below in table 6:

TABLE 6

| Time (min) | Marketed formulation | Formulation 3 |
|---|---|---|
| 10 | 67 | 41 |
| 15 | 85 | 68 |
| 20 | 93 | 81 |
| 30 | 98 | 92 |
| 45 | 99 | 98 |

Conclusion: Thus, it is concluded that the release profile of formulation of present invention comprising 11.0% lecithin showed comparative dissolution profile to marketed formulation.

It will be readily apparent to one skilled in the art that varying substitutions and modifications may be made to the invention disclosed herein without departing from the spirit of the invention. Thus, it should be understood that although the present invention has been specifically disclosed by the preferred embodiments and optional features, modification and variation of the concepts herein disclosed may be resorted to by those skilled in the art, and such modifications and variations are considered to be falling within the scope of the invention.

It is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It must be noted that, as used in this specification and the appended claims, the singular forms "a," "an" and "the" include plural references unless the context clearly dictates otherwise. Thus, for example, reference to a "cosolvent" refers to a single cosolvent or to combinations of two or more cosolvents, and the like.

What is claimed is:

1. A pharmaceutical dosage form which comprises a soft gelatin capsule for oral administration, wherein the soft gelatin capsule comprises a pharmaceutical formulation comprising a suspension of the following components:

a carrier system comprising phospholipids and medium chain triglycerides or mixtures thereof, wherein the phospholipids are lecithins and are present in an amount of 11% to 20% by weight of the total formulation, and wherein the medium chain triglyceride is present in an amount of 25% to 40% w/w of the total formulation;

a therapeutically effective amount of nintedanib or its pharmaceutically acceptable salt, wherein the nintedanib or pharmaceutically acceptable salt thereof is present in an amount of about 30% to about 50% w/w of the total formulation, and wherein the nintedanib or its pharmaceutically acceptable salt is present partially in the form of finely divided particles suspended in the carrier system and partially in the form of a solution; and optionally including additional pharmaceutically acceptable excipients.

2. The dosage form of claim 1, wherein the nintedanib or pharmaceutically acceptable salt thereof comprises nintedanib esylate salt.

3. The dosage form of claim 1, wherein the carrier system further comprises a surfactant, a solubilizing agent, an emulsifying agent, a thickener, or mixtures thereof.

4. The dosage form of claim 3, wherein the surfactants are selected from the group consisting of: polyoxyethylene castor oil derivatives, polyoxyethylene polyoxypropylene block copolymers, polyoxyethylene polypropylene glycol, a mono fatty acid ester of polyoxyethylene sorbitan, polyoxyethylene sorbitan monostearate, polyoxyethylene sorbitan monopalmitate, polyoxyethylene sorbitan monolaurate, propylene glycol monolaurate, propylene glycol dicaprylate, sorbitan laurate, sorbitan monostearate, caprylocaproyl macrogolglyceride, octadecanoic acid, sorbitan oleate, sorbitan palmitate, sorbitan stearate, propylene glycol monocaprylate, soyabean oil, vegetable oil, triacetin, triethyl citrate, macrogolglycerol-hydroxystearate, macrogolglycerol-ricinoleate, and mixtures thereof.

5. The dosage form of claim 4, wherein the surfactants are selected from polyoxyl castor oil, caprylocaproyl macrogolglyceride, or octadecanoic acid and are present in an amount of 10% to 30% w/w of the total formulation.

6. The dosage form of claim 3, wherein the thickener is selected from the group consisting of: polyethylene glycols, colloidal silica, bees wax, glycerol monostearate, hydrogenated vegetable oil, partially hydrogenated vegetable oil, and a hard fat.

7. The dosage form of claim 6, wherein the thickener is hard fat present in an amount of 10% to 30% w/w of the total formulation.

8. The dosage form of claim 1, further comprising a solubilizing agent selected from the group consisting of: lineleoyl polyoxyl-6-glycerides, corn oil mono glycerides, corn oil di glycerides, corn oil triglycerides, and mixtures thereof.

9. The dosage form of claim 8, wherein the solubilizing agent is present in an amount of less than 10% w/w of the total formulation.

10. The dosage form of claim 1, further comprising phosphatidylcholine and a solvent in an amount of about 1% to 50% w/w of the total formulation.

11. The dosage form of claim 1, wherein the carrier system further comprises a pharmaceutically acceptable nonphospholipid surfactant, wherein the pharmaceutically acceptable nonphospholipid surfactant comprises polysorbate 80, polysorbate 20, Vitamin E TPGS, or d-a-tocopheryl polyethylene glycol 1000 succinate in an amount of 1% to about 25% w/w of the total formulation.

12. A lipid suspension comprising:
   a carrier system comprising:
      25% to 40% medium chain triglycerides by weight of the suspension;
      10% to 30% of hard fat by weight of the suspension; and
      11% to 20% of lecithin by weight of the suspension; and
   nintedanib esylate in an amount of 30% to 50% by weight of the suspension, wherein the nintedanib esylate is present partially in the form of finely divided particles and suspended in the carrier system and partially in the form of a solution.

13. A lipid suspension of claim 12, wherein the lecithin is present in an amount of 11% by weight of the suspension.

* * * * *